United States Patent [19]

Lessard et al.

[11] Patent Number: 5,397,708
[45] Date of Patent: Mar. 14, 1995

[54] METHOD FOR DETECTION OF SULFIDES

[75] Inventors: Ronald B. Lessard, Sugarland, Tex.; Manian Ramesh, Naperville, Ill.

[73] Assignee: Nalco Chemical Company, Naperville, Ill.

[21] Appl. No.: 62,413

[22] Filed: May 13, 1993

[51] Int. Cl.$^6$ .............................................. G01N 33/24
[52] U.S. Cl. ........................................ 436/30; 436/25; 436/81; 436/150; 546/99; 548/549
[58] Field of Search ............... 436/30, 81, 150, 25; 422/5; 546/99; 548/548, 549

[56] References Cited

U.S. PATENT DOCUMENTS

| | | | |
|---|---|---|---|
| Re. 33,349 | 9/1990 | Matza et al. | 175/40 |
| 4,124,475 | 11/1978 | Zetter et al. | 204/195 R |
| 4,154,659 | 5/1979 | Zetter | 204/1 T |
| 4,154,660 | 5/1979 | Micko | 204/1 T |
| 4,157,283 | 6/1979 | Zetter | 204/1 T |
| 4,252,655 | 2/1981 | Carney | 252/8.5 C |
| 4,569,766 | 2/1986 | Kool et al. | 210/690 |
| 4,680,127 | 7/1987 | Edmondson | 210/749 |
| 4,740,475 | 4/1988 | Paul | 436/165 |
| 4,805,708 | 2/1989 | Matza et al. | 175/40 |
| 4,840,910 | 6/1989 | Matza et al. | 436/30 |
| 4,844,877 | 7/1989 | Leder | 423/226 |
| 5,008,022 | 4/1991 | Leder | 210/755 |
| 5,082,576 | 1/1992 | Howson | 507/130 |
| 5,128,049 | 7/1992 | Gatlin | 210/752 |
| 5,206,519 | 4/1993 | Kirk | 250/565 |
| 5,548,720 | 10/1985 | Gilligan, III | 252/8.5 B |

OTHER PUBLICATIONS

Aldrich Chemical Company, Catalog Handbook of Fine Chemicals, 1992–1993, p. 833.

*Primary Examiner*—James C. Housel
*Assistant Examiner*—Harold Y. Pyon
*Attorney, Agent, or Firm*—Hill, Steadman & Simpson

[57] ABSTRACT

A method for determining the concentration of sulfide in a process stream. The method comprises the steps of adding to a process stream a sulfide scavenger (probe) that changes electronic properties when it reacts with sulfide. One can then monitor the electronic properties of the sulfide scavenger in the process stream to determine the concentration of sulfide present. In a preferred embodiment, the sulfide scavenger is either fluorescent and when it reacts with sulfide becomes inactive or is inactive and when it reacts with sulfide becomes fluorescent.

1 Claim, 1 Drawing Sheet

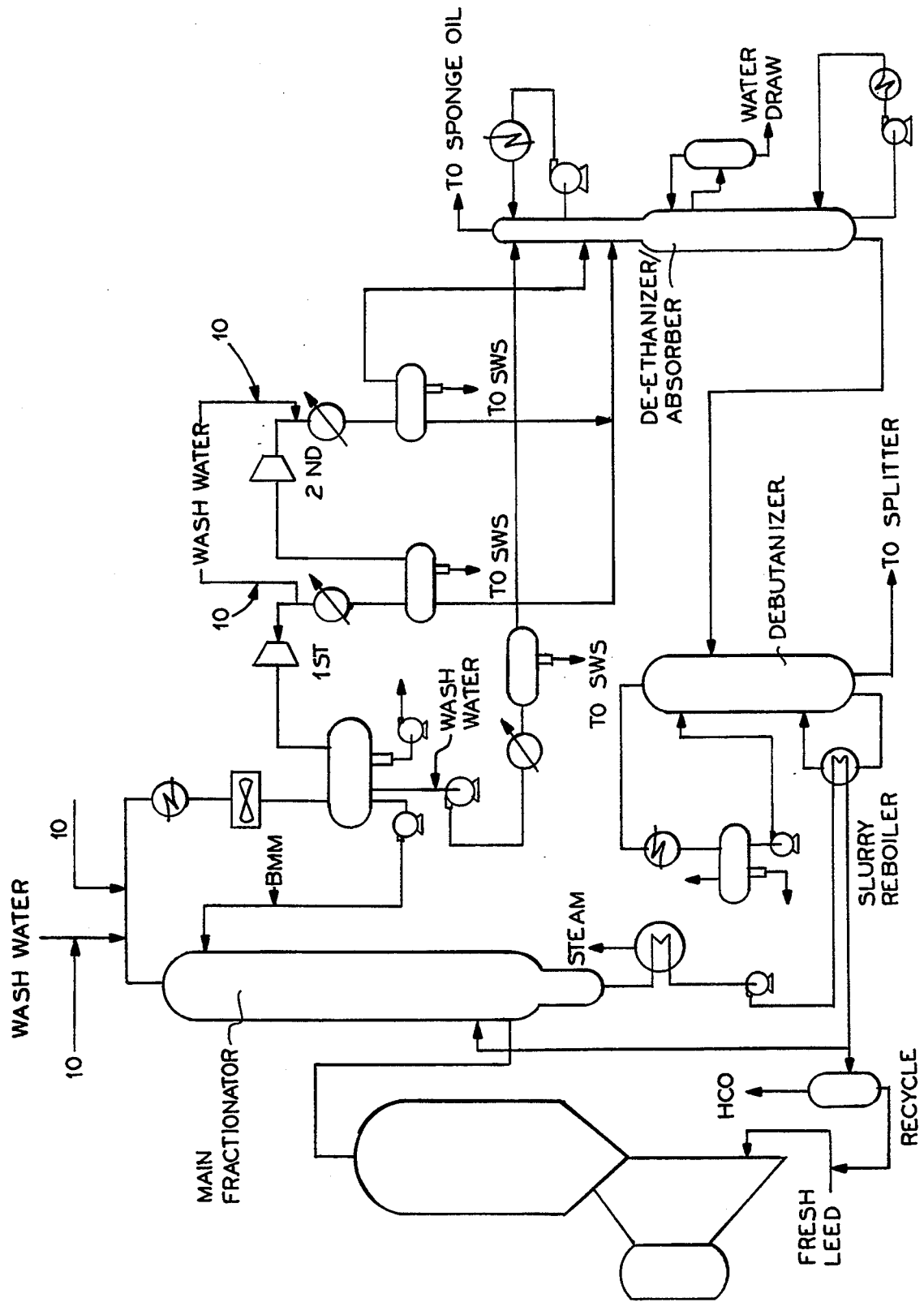

METHOD FOR DETECTION OF SULFIDES

BACKGROUND OF THE INVENTION

The present invention relates generally to the removal of sulfides from a process stream. More specifically, the present invention provides a method for determining the concentration of sulfides in a process stream.

Sulfides are generated in many aspects of the oil production and refinery industry. Sulfides can be generated in the oil fields where oil is collected as well as at the refinery wherein the oil is processed.

Due to the health hazards associated with the exposure to sulfides, it is important to remove sulfides from process streams in the oil field. Additionally, sulfides can also cause metal fatigue in crude units, and therefore must be removed; sulfides can cause hydrogen blistering in oil refineries.

Although methods do exist for removing sulfides from such process streams, these systems do not function entirely satisfactorily. Examples of sulfide scavengers include compounds chosen from a class of chemicals referred to as "aminals." These sulfide scavengers include bis-morpholinyl methane and N,N,N',N'-tetra alkyl diamino methane.

Although these sulfide scavengers provide compositions that can remove sulfides from a process stream, an issue arises as how to determine how much scavenger to use. Of course, if a sufficient amount of sulfide scavenger is not used, sulfide will remain in the process stream. On the other hand, if excessive amounts of sulfide scavenger are used, costs are unnecessarily increased and potential processing problems can result from the excess scavenger.

One method for the on-line detection of sulfide involves a system that employs the use of lead acetate paper. The lead acetate reacts with the sulfide and creates lead sulfide. A device is employed that determines the concentration of lead sulfide that is formed. This system is extremely expensive, with a cost of more than $50,000.00.

Additional methods for determining sulfide concentration include the use of near infrared detection. Additionally, sulfur specific chromatography is sometimes used. However, there are also disadvantages inherent with these systems. Houston Atlas, a Baker Hughes company, provides instrumentation that utilizes the lead acetate detection method. Additionally, sulfur specific chromatography is provided by Houston Atlas.

SUMMARY OF THE INVENTION

The present invention provides an improved method for determining the concentration of sulfide in a process stream. The method comprises the steps of adding to a process stream a sulfide scavenger that changes electronic properties when it reacts with sulfide (hereinafter referred to as "probe"). One can then monitor the electronic properties of the probe in the process stream to determine the concentration of sulfide present.

In a preferred embodiment, the probe is either fluorescent and when it reacts with sulfide becomes inactive or is inactive and when it reacts with sulfide becomes fluorescent. It is also possible that the probe emits light of a certain wavelength before reacting with sulfide, and after it reacts with the sulfide emits light of a different wavelength.

In a preferred embodiment, the probe has the general structure R—N—CH$_2$—N—R' wherein R and R' are chosen from the group consisting of fluorescent aromatic or heteroaromatic amines.

In an embodiment, the probe is a fluorescent maleimide.

The electronic properties of the probe can be detected with either an absorption or emission based instrument.

The present invention also provides a method for removing sulfide from a fluid stream comprising the steps of: collecting a sample of fluid; determining the amount of sulfides in the fluid by adding to the fluid a compound that changes electronic properties when it reacts with sulfide; monitoring the electronic properties of the compound and generating a signal in response; and adding a traditional sulfide scavenger to the fluid stream based on the signal that is generated.

In an embodiment, the method includes the step of first adding to the fluid stream a sulfide scavenger, such as bis-morpholinyl methane, and then collecting a sample of fluid. The probe is then added to the fluid stream. As necessary, further sulfide scavenger is then added to the fluid stream in response to the signal that is generated by the probe.

An advantage of the present invention is that it provides an improved method for determining the concentration of sulfide in a fluid stream.

A further advantage of the present invention is that it provides an improved method for removing sulfides from a fluid stream.

Additionally, an advantage of the present invention is that it provides an on-line method for determining the concentration of sulfide in an oil refinery.

Moreover, an advantage of the present invention is to provide a system that allows automatic/continuous monitoring of the concentration of sulfides in overhead water.

Still further, an advantage of the present invention is that it provides a method that can be connected to a sulfide scavenger system and allows the amount of sulfide scavenger that is added to a fluid stream to be varied as the sulfide concentration changes.

Furthermore, an advantage of the present invention is that it results in better process control and less plant down time.

Additional features and advantages of the present invention are described in, and will be apparent from, the detailed description of the presently preferred embodiments and from the drawing.

BRIEF DESCRIPTION OF THE DRAWING

The FIGURE illustrates a schematic of a refinery process.

DETAILED DESCRIPTION OF THE PRESENTLY PREFERRED EMBODIMENTS

The present invention provides an improved method for determining the concentration of the sulfide in a fluid stream. Although in the preferred embodiment the method is set forth for use in an oil refinery, the method can be used to detect sulfide levels in other fluids.

Pursuant to the present invention, compounds are utilized that change electronic properties when they react with sulfide. These compounds or probes are sulfide scavengers that provide an easy method for determining the concentration of sulfides in a process stream. To provide clarity to the specification and to avoid confusion herein with respect to traditional sulfide scavengers, such as bis-morpholinyl methane, the sulfide scavengers that change electronic properties of the present invention will be referred to herein as "probes."

The method of the present invention provides an on-line system that can automatically determine the concentration of sulfide. This allows one to control the rate of sulfide scavenger addition. As previously noted, traditionally, sulfide scavengers, such as bismorpholinyl methane, are added to fluid streams to remove or neutralize sulfide.

Referring to the Figure, a general flow diagram, or schematic, involving a main fractionator and accompanying equipment is illustrated. The equipment includes a slurry reboiler, a debutanizer, a de-ethanizer absorber, various condensers, storage vessels, pipelines, pumps, and heaters. Specifically, the flow of fluid through a refinery system including a main fractionator is illustrated.

Pursuant to the present invention, a probe that changes electronic properties when it reacts with sulfide is added to the system. The probe can be added at a number of locations in the system indicated, for example, by 10 on the Figure. Likewise, at these locations, typical sulfide scavengers, such as bis-morpholinyl methane can also be added to neutralize the sulfide.

Pursuant to the present invention, the probe that changes electronic properties when it reacts with sulfide is added to the fluid stream. Preferably, the probe is either fluorescent and becomes inactive when it reacts with sulfide or is inactive and becomes active when it reacts with sulfide.

In an embodiment, preferably, the probe has the general structure:

wherein:

R and R' are fluorescent aromatic or heteroaromatic amines. R and R' may or may not be the same.

The R groups are the absorbing units. Due to the reaction of the R groups with sulfide, this will lead to a change in absorption and/or emission.

To create a probe having the general structure R—N—CH₂—N—R', the general following reaction can be used:

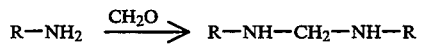

The following general reaction occurs with the sulfide.

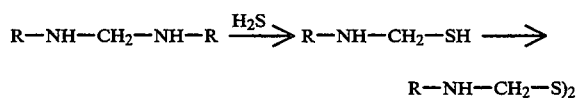

By way of example, and not limitation, examples of probes that can be utilized are as follows:

EXAMPLE NO. 1

6-aminoquinoline is reacted with formaldehyde to create

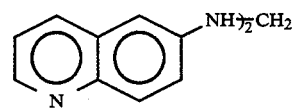

which is fluorescent inactive. When this compound reacts with sulfide it creates a fluorescent active product pursuant to the following reaction.

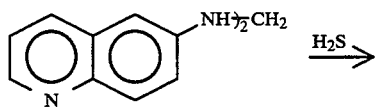

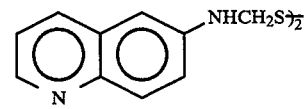

which is fluoroactive.

EXAMPLE NO. 2

6-aminocoumarin is reacted with formaldehyde to create

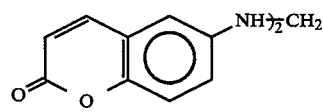

which is fluoroactive. When this reacts with sulfide, it creates a fluoroinactive product pursuant to the following reaction.

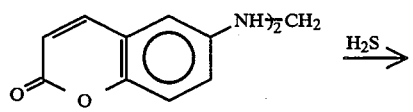

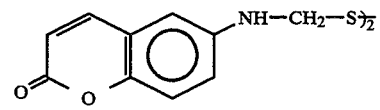

which is fluoroinactive.

EXAMPLE NO. 3

Fluorescent maleimides can be used as probes (sulfide scavengers) pursuant to the present invention. Examples of these compounds are set forth below. N-(1-pyrene) maleimide and CPM are oil soluble and disodium salt of the disulfonic acid is water soluble. These maleimides are generally non-fluorescent until they react with thiols.

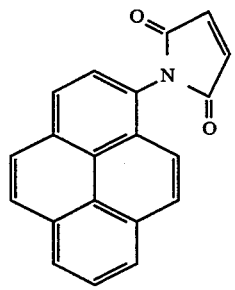

N-(1-pyrene)maleimide

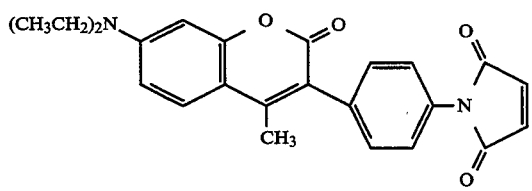

7-diethylamino-3-(4'-maleimidylphenyl)-4-methylcoumarin (CPM)

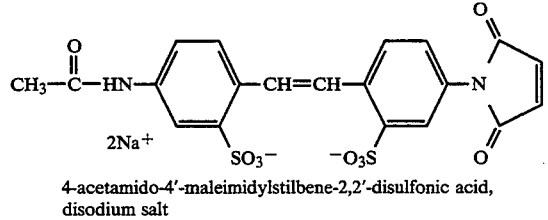

4-acetamido-4'-maleimidylstilbene-2,2'-disulfonic acid, disodium salt

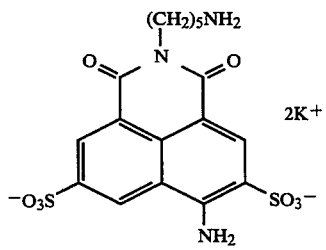

N-(5-aminopentyl)-4-amino-3,6-disulfo-1,8-naphthalimide, dipotassium salt (Lucifer Yellow cadaverine)

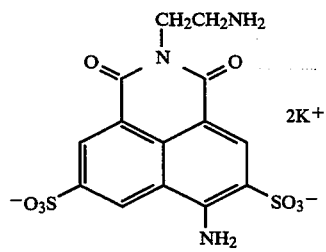

N-(2-aminoethyl)-4-amino-3,5-disulfo-1,8-naphthalimide, dipotassium salt

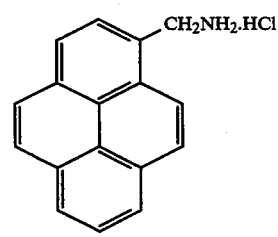

1-aminomethylpyrene, hydrochloride

-continued

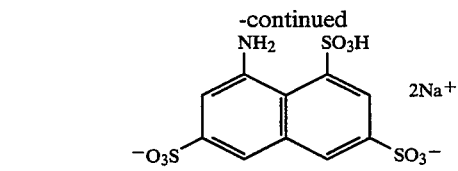

8-aminonaphthalene-1,3,6-trisulfonic acid, disodium salt (ANTS)

The system of the present invention will allow one to control the rate of sulfide scavenger addition. To this end, the result of the reaction between the probe and the sulfide will provide the concentration of the sulfide present in the fluid stream. By using the concentration of sulfide present, the feed rate of scavenger can then be automatically adjusted to insure sufficient sulfide scavenger is added to the fluid. On the other hand, because of the accuracy of the measurement excess sulfide scavenger need not be added.

Examples of such scavengers are:

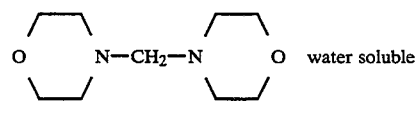

(bis morpholinyl methane)

and

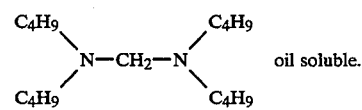

oil soluble.

In an embodiment, in use, a sample is taken from the fluid stream and the probe is used to determine the amount of sulfide contained in the sample taken from the fluid stream. The probe is then added to the fluid stream in an amount that is 150 to 200% of the sulfide content as determined from the sample. The excess probe is desirable to deal with increases in sulfide content in the fluid stream. Generally, the probe will be added in an amount of approximately 1 to about 500 ppm.

The change in electrical properties of the probe in the fluid stream is then measured. Because the intensity of light generated by the probe is in proportion to the amount of sulfide, overloading the system with probe does not adversely effect the measurements. However, the probe will provide an accurate determination of sulfide content allowing accurate dosage to stoichiometry levels.

In order to detect the change in electrical properties of the probe, downstream, from the addition of the probe to the fluid stream, a portion of the fluid stream will be diverted through typical valve and pump means. This portion of the fluid stream will then be subjected to either absorption or emission light detection. A number of different products can be used including, for example, a Turner Model 10-AU-000 or Hitachi F-1200 portable fluorescent spectrometer. Typically, these devices comprise a lamp or LED and photodiode or photomultiplier tube.

Due to the characteristics of the probes used in the present invention, the resultant probe, i.e., the probe after it is added to a fluid stream including sulfide, will absorb light differently than it did before addition to the stream. The difference in light absorption can be used to determine sulfide concentration. This data will be used through a PC or other means, to calculate the sulfide scavenger to be added to the stream.

By way of example, and not limitation, experiments demonstrating the use of the invention will now be given.

Investigations:

Pyrenemaleimide was used as a probe in the studies. The following is a representative example of the investigation:

In a 50 mL round bottomed flask sodium sulfide (1000 ppm) and ethyl alcohol (50 mL) was taken and kept well stirred. To this a solution of pyrenemaleimide (1000 ppm) was added. The mixture was then heated at 30° C. for 15 minutes.

Thin layer chromatography of the reaction mixture indicated the complete disappearance of pyrenemaleimide and the formation of two main products. These products were separated and identified to be N-(1-pyrene) succinimido-3-thiol and the corresponding disulfide.

Fluorescence Measurements:

Steady-state fluorescence spectra were recorded on a Gilford Fluoro IV spectrometer. Excitation spectra were measured in the ratio mode. Emission spectra were not corrected. For measurements of $I_1/I_3$ ratio, the ratio of the intensity of NDSA fluorescence intensity of peak 3 (330) to peak 1 (240) was used.

Fluorescence data:

N-(1-pyrene)maleimide: Abs=339 nm; EM=376,396 nm; Ex (Extinction Coefficient)=$36 \times 10^{-3}$ Cm$^{-1}$M$^{-1}$ Sulfur addition products:

$Abs = 360$ nm;

$EM = 443$ nm;

$Ex = 3.7 \times 10^{-3}$ Cm$^{-1}$M$^{-1}$

In a second approach, a fluorescent amine was reacted with formaldehyde. The resulting aminal was used as a H$_2$S scavenger in a fashion identical to bis-Morpholinyl methane.

Preparation of Fluorescent scavenger:

In a 50 mL reaction flask N-[2-aminoethyl)-4-amino-3,6-disulfo-1,8-naphthalimide dipotassium salt (0.2 mole) and DMF (10 mL) was taken. The contents of the flask were stirred well, and paraformaldehyde (0.1 mole) was added. The reaction mixture was heated at 110° C. for 2.5 hrs. It was then cooled and the product was isolated by triturating with methylene dichloride. The product obtained was identified to be bis-(N-[2-aminoethyl)-4-amino-3,6-disulfo-1,8-naphthalimide)methane dipotassium salt.

Hydrogen sulfide abatement:

In a 60 mL round bottomed flask sodium sulfide (1000 ppm) and water (50 mL) was taken and kept well stirred. To this, bis-(N-[2-aminoethyl]-4-amino-3,6-disulfo-1,8-naphthalimide)methane dipotassium salt (1000 ppm) was added. The mixture was then heated at 80° C. for 15 minutes. Thin layer chromatography of the reaction mixture indicated the complete disappearance of naphthalimide. The main product was separated and identified to be bis N-(1-thio-2-aminoethyl)4-amino-3,6-disulfo-1,8-naphthalimide dipotassium salt.

Fluorescence data:

(N-[2-aminoethyl)-4-amino-3,6-disulfo-1,8-naphthalimide dipotassium salt $Abs = 425$ nm;

$EM = 530$ nm;

$Ex = 13 \times 10^{-3}$ Cm$^{-1}$M$^{-1}$ bis-(N-[2-aminoethyl]-4-amino-3,6-disulfo-1,8-naphthalimide)methane dipotassium salt:

$Abs = 424$ nm;

$EM = 530$ nm;

$Ex = 13 \times 10^{-3}$ Cm$^{-1}$M$^{-1}$ bisN-(1-thio-2-aminoethyl)4-amino-3,6-disulfo-1,8-naphthalimide dipotassium salt:

$Abs = 560$ nm;

$EM = 581$ nm;

$EX = 96 \times 10^{-3}$ Cm$^{-1}$M$^{-1}$

These experiments demonstrate that the sulfide scavengers can be used to monitor the sulfide content in the fluid stream.

The reactions that occur in methods I and II are as follows:

METHOD I

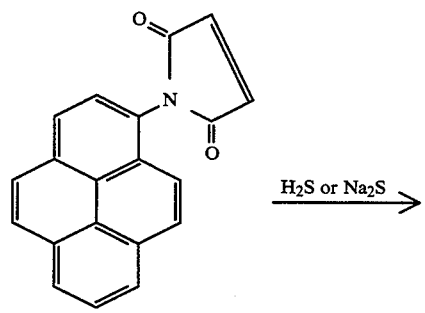

H$_2$S or Na$_2$S →

NON FLUORESCENT

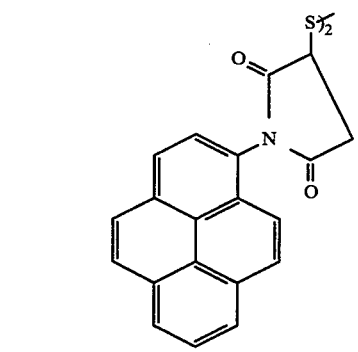

FLUORESCENT

METHOD II

-continued

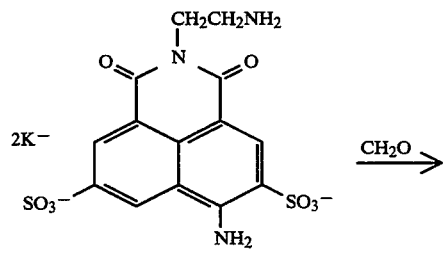

FLUORESCENT

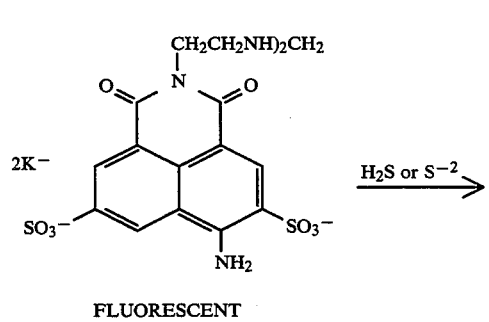
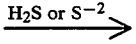

FLUORESCENT

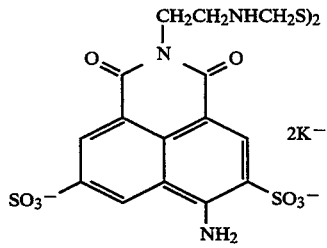

-continued

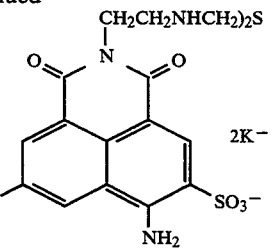

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for determining the concentration of sulfide in a fluid comprising the steps of:
   collecting a fluid;
   adding to the collected fluid a compound that changes electronic properties when it reacts with sulfides; and
   monitoring the electronic properties of the compound in the collected fluid;
   wherein the compound is chosen from the group consisting of:

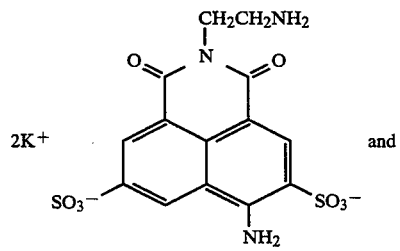

and

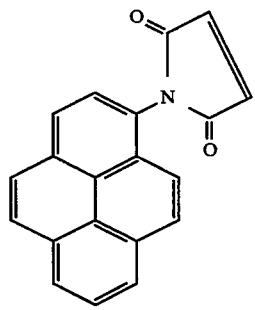

* * * * *